United States Patent [19]

Weeks

[11] Patent Number: 4,483,982
[45] Date of Patent: Nov. 20, 1984

[54] PROCESSES FOR PREPARING PIROXICAM AND INTERMEDIATES LEADING THERETO

[75] Inventor: Paul D. Weeks, Gales Ferry, Conn.

[73] Assignee: Pfizer Inc., New York, N.Y.

[21] Appl. No.: 596,568

[22] Filed: Apr. 5, 1984

Related U.S. Application Data

[63] Continuation of Ser. No. 413,036, Sep. 2, 1982, , Continuation-in-part of Ser. No. 308,746, Oct. 5, 1981, Pat. No. 4,376,204.

[51] Int. Cl.$^3$ .......................................... C07D 279/02
[52] U.S. Cl. ...................................... 544/49; 548/210
[58] Field of Search ........................... 544/49; 548/210

[56] References Cited

U.S. PATENT DOCUMENTS

| | | | |
|---|---|---|---|
| 3,591,584 | 7/1971 | Lombardino | 424/246 |
| 3,853,862 | 12/1974 | Lombardino | 544/49 |
| 3,891,637 | 6/1975 | Lombardino | 424/246 |
| 4,116,964 | 9/1978 | Zinnes et al. | 548/210 |
| 4,376,204 | 3/1983 | Weeks | 548/210 |

OTHER PUBLICATIONS

Barton and Ollis, *Comprehensive Organic Chemistry*, vol. 4, Pergamon, New York, (1979), pp. 1093–1095.
Lombardino et al., "Synthesis . . . 2H–1,2–Benzothiazine 1,1 Dioxide," J. Med. Chem. 14, pp. 1171–1175, (1971).

*Primary Examiner*—Nicholas S. Rizzo
*Assistant Examiner*—G. Hendricks
*Attorney, Agent, or Firm*—Charles J. Knuth; Albert E. Frost; James M. McManus

[57] ABSTRACT

Processes for the preparation of the antiinflammatory agent piroxicam and intermediates leading thereto, the first of which comprises reacting N-methylsaccharin with (N-2-pyridyl)haloacetamides and alkyl haloacetates in the presence of an appropriate base to give, respectively, piroxicam and alkyl 4-hydroxy-2-methyl-2H-1,2-benzothiazine-3-carboxylate 1,1-dioxides, intermediates which can be converted into piroxicam; and the second of which comprises reacting a novel alkyl 2-(2-methyl-3-hydroxy-2,3-dihydro-1,2-benzisosulfonazol-3-yl)-2-haloacetate with a metal hydride to give alkyl 4-hydroxy-2-methyl-2H-1,2-benzothiazine-3-carboxylate 1,1-dioxides, intermediates leading to piroxicam.

16 Claims, No Drawings

PROCESSES FOR PREPARING PIROXICAM AND INTERMEDIATES LEADING THERETO

CROSS REFERENCE TO RELATED APPLICATION

This application is a continuation of co-pending application Ser. No. 413,036, filed Sept. 2, 1982, which is a continuation-in-part of copending application Ser. No. 308,746, filed Oct. 5, 1981 now U.S. Pat. No. 4,376,204.

FIELD OF THE INVENTION

This invention relates to novel processes leading to the antiinflammatory agent piroxicam and to certain intermediates which can be converted to piroxicam.

DESCRIPTION OF THE ART

Piroxicam, a potent antiinflammatory agent, was first reported by Lombardino in U.S. Pat. No. 3,591,584. One of the processes for the synthesis of piroxicam disclosed therein is to react a 3-carboxylic acid ester with 2-aminopyridine. More specifically, the ester is disclosed as a ($C_1$-$C_{12}$) alkyl ester or phenyl($C_1$-$C_3$)alkyl ester. The specific ester described is the methyl ester, viz.,

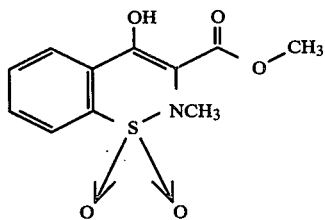

[See also Lombardino et al., J. Med. Chem. 14, pp. 1171–1175 (1971)].

In a more recent U.S. patent application (Ser. No. 191,716, filed Sept. 29, 1980) it is taught that the corresponding 2-methoxyethyl ester can be used in place of the methyl ester in its reaction with 2-aminopyridine with certain advantages.

Other alternative syntheses of piroxicam which have been disclosed in the literature include reaction of 3,4-dihydro-2-methyl-4-oxo-2H-1,2-benzothiazine 1,1-dioxide with 2-pyridyl isocyanate (Lombardino, U.S. Pat. No. 3,591,584), transamidation of 4-hydroxy-2-methyl-2H-1,2-benzothiazine-3-carboxanilides with 2-aminopyridine (Lombardino, U.S. Pat. No. 3,891,637), cyclization of

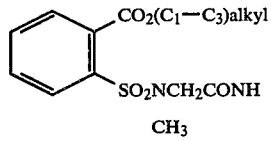

(Lombardino, U.S. Pat. No. 3,853,862), coupling of a 4-($C_1$-$C_3$)alkoxy-2-methyl-2H-1,2-benzothiazine-3-carboxylic acid 1,1-dioxide with 2-aminopyridine followed by hydrolysis of the enolic ether linkage (Lombardino U.S. Pat. No. 3,892,740), coupling of 4-hydroxy-2-methyl-2H-1,2-benzothiazine-3-carboxylic acid, via the acid chloride, with 2-aminopyridine (Hammen, U.S. Pat. No. 4,100,347) and methylation of 4-hydroxy-N-2-pyridyl-2H-1,2-benzothiazine-3-carboxamide (Canada Pat. No. 1,069,894).

SUMMARY OF THE INVENTION

It has now been discovered that a compound selected from the formula

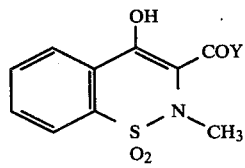

where Y is alkoxy of one to four carbon atoms, 2-methoxyethoxy or 2-pyridylimino can be prepared by reaction a compound of the formula

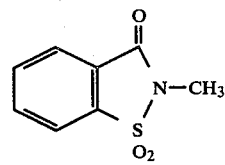

with a compounds selected from the formula

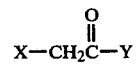

wherein X is chloro, bromo or iodo in a polar, reaction-inert solvent in the presence of at least two equivalents of a base selected from the group consisting of a metal hydride, an alkali metal alkoxide having one to four carbon atoms, potassium hexamethyl disilazane and potassium diisopropylamine at a temperature of from about 25° C. to about 70° C. until the reaction is substantially complete.

A preferred feature of this process is the use of a reaction-inert solvent selected from dimethylformamide, dimethylacetamide, dimethylsulfoxide, hexamethylphosphoramide and 1-methyl-2-pyrrolidone.

A further preferred feature of this process is the use of a metal hydride selected from potassium hydride, sodium hydride and calcium hydride.

An especially preferred feature of the present process is the use of the compound X—$CH_2$CO—Y wherein X is chloro or bromo, the reaction-inert solvent is dimethylformamide or dimethylsulfoxide, the metal hydride is sodium hydride and Y is methoxy, 2-methoxyethoxy or 2-pyridylimino. A second especially preferred feature of this process is the use of dimethylsulfoxide as solvent and potassium hexamethyl disilazane as the base, and wherein Y is methoxy and X is chloro.

Another preferred feature of this process is the use of the aforementioned preferred solvents wherein the base is an alkali metal alkoxide having one to four carbon atoms. Especially preferred is the use of potassium t-butoxide as the base and dimethylsulfoxide as the solvent wherein X is chloro and Y is methoxy.

Those compounds of this process where Y is said alkoxy and methoxyethoxy are useful intermediates leading to piroxicam as described in the aforementioned art references, while the compound where Y is 2-pyridylimino is piroxicam, a useful antiinflammatory agent.

This process offers distinct advantages over other processes leading to piroxicam and intermediates thereto since the methylation step of the 4-hydroxy-2H-1,2-benzothiazine ring system is avoided, the methyl group being introduced in the readily available N-methylsaccharin starting material. In addition, this process provides the desired products in a high yield one-step process.

Also a part of the present invention is a process for preparing compounds selected from the formula

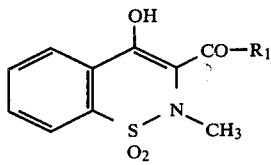

wherein $R_1$ is alkoxy of one to four carbon atoms or 2-methoxyethoxy which comprises reacting a compound selected from the formula

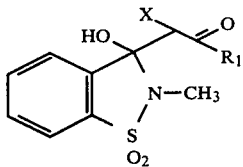

wherein X is chloro, bromo or iodo with one equivalent of a metal hydride in a polar, reaction-inert solvent at from about 25° C. to about 50° C. until the reaction is substantially complete.

A preferred feature of this process is the use of a reaction-inert solvent selected from dimethylformamide, dimethylacetamide, dimethylsulfoxide, hexamethylphosphoramide and 1-methyl-2-pyrrolidone.

Another preferred feature of this process is the selection of a metal hydride from potassium hydride, sodium hydride and calcium hydride.

An especially preferred feature of this process is the use of a starting reagent wherein X is chloro, the reaction-inert solvent is dimethylformamide or dimethylsulfoxide, the metal hydride is sodium hydride and $R_1$ is methoxy or 2-methoxyethoxy.

The compounds of this process are useful intermediates leading to piroxicam as described in the aforementioned art references.

This process has the advantages of providing the desired products in high yield and also precludes the necessity for methylation of the 4-hydroxy-2H-1,2-benzothiazine ring system.

Also included in the scope of the present invention are novel starting reagents for the above described process of the formula

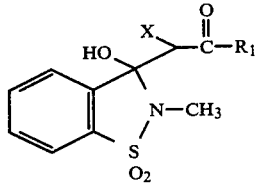

where X is chloro, bromo or iodo; and $R_1$ is alkoxy of one to four carbon atoms or methoxyethoxy.

Preferred compounds in this series are those where X is chloro and $R_1$ is methoxy or 2-methoxyethoxy.

As one skilled in the art can readily recognize the compounds prepared by the instantly claimed processes can exist in either the ketonic or enolic tautomeric form:

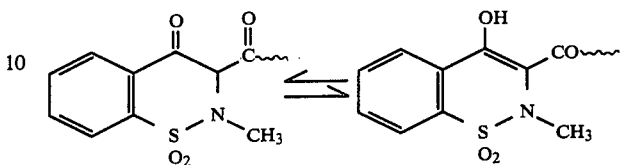

Those skilled in the art will understand that these forms are equivalent. The present invention is intended to encompass both tautomeric forms while writing only one of them as a matter of convenience.

DETAILED DESCRIPTION OF THE INVENTION

The first process of the present invention leading to the synthesis of the antiinflammatory agent piroxicam and intermediates useful in the preparation of this agent through an aminolysis reaction can be depicted as follows:

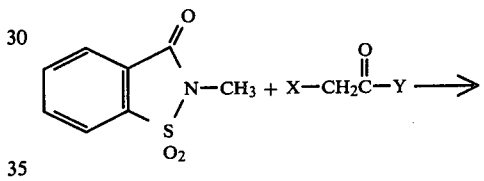

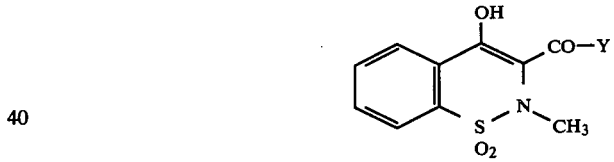

where X and Y are as previously defined.

The process comprises the reaction of one mole of N-methylsaccharin with one mole of a haloacetate or haloacetamide derivative. Although equimoles of the reactant are required it is preferred, for optimum yields, that an excess of the haloacetate or haloacetamide be employed. It is further preferred that as much as 100% excess of these reagents be used. Larger amounts can be employed, but have little if any affect on the yield of the product.

Also utilized in this process for condensing N-methylsaccharin and haloacetate or haloacetamide derivatives is a metal hydride. For each mole of N-methylsaccharin two equivalents of a metal hydride are employed. Any metal hydride can be employed, although alkali metal hydrides are preferred since many are commercially available or can be readily prepared.

In addition to metal hydrides, other bases, when used in the manner prescribed for the metal hydrides, also facilitate the condensation reaction of this process. These include alkali metal alkoxides, potassium hexamethyl disilazane and potassium diisopropylamine.

The present process is also conducted in a reaction-inert solvent. Such a solvent, or mixtures thereof, should solubilize the reactants to such an extent that the reaction is facilitated, but not reacted with the reactants or product to any appreciable extent. Such solvents should also be highly polar, having a dielectric constant (e) of $\geq 35$. These include such preferred solvents as dimethylformamide, dimethylacetamide, hexamethylphosphoramide, dimethylsulfoxide and 1-methyl-2-pyrrolidone.

Regarding the manner in which the reagents are combined, it is preferred that the metal hydride be added to a solution of the reactants in the reaction-inert solvent. In practice, the hydride is added to the reaction mixture, preheated to the desired reacting temperature, over a period of one to two hours, or at such a rate that the heat formed during the addition of the hydride does not cause overheating of the reaction mixture.

Concerning reaction temperature, the present process can be conducted at an ambient temperature of about 25° C. to about 70° C. Reaction temperatures lower or higher than the preferred temperature range will provide product, but will have a deleterious affect on the product, and offer no distinct advantages. Following the addition of the metal hydride, the reaction temperature is maintained for two to six hours to ensure completion of the reaction.

On completion of the reaction mixture is quenched in cold 5% hydrochloric acid and the product either filtered and dried or extracted into a water immiscible solvent such as methylene chloride. The product, after filtration and drying or after removal of the extracting solvent, can be purified by conventional means, or can be employed in subsequent steps leading to piroxicam without purification.

The second process of the present invention leading to intermediates useful in the synthesis of the antiinflammatory agent piroxicam can be depicted as follows:

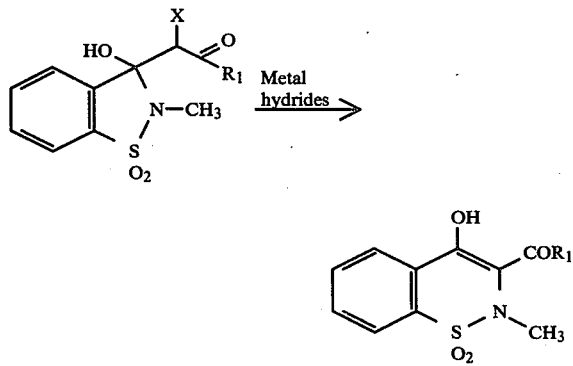

wherein X and $R_1$ are as previously defined.

The process comprises reacting one mole of an appropriate 1,2-benzisosulfonazole with an equivalent of a metal hydride in a polar reaction-inert solvent. Any metal hydride can be used, although alkali metal hydrides and alkaline earth metal hydrides are preferred as many are commercially available or can be readily prepared. Especially preferred are sodium hydride, potassium hydride and calcium hydride.

The present process is also carried out in a reaction-inert solvent. Such a solvent, or mixtures thereof, should solubilize the reactants to such a degree that the reaction is facilitated, but should not react with the reagents or the product to any appreciable extent. Such solvents should also be highly polar solvents having a dielectric constant (e) of $\geq 35$. These include such preferred solvents as dimethylsulfoxide, dimethylformamide, dimethylacetamide, 1-methyl-2-pyrrolidone and hexamethylphosphoramide.

Regarding the combining of the reagents, the appropriate metal hydride can be added to the requisite 1,2-benzisosulfonazole in a reaction-inert solvent, or the 1,2-benzisosulfonazole in the reaction-inert solvent can be added to a suspension of the metal hydride in the reaction-inert solvent.

Following the combining of the reagents, the reaction is heated to the reaction temperature of from about 25° C. to about 50° C. Reaction temperatures lower or higher will provide product, but will have a deleterious affect on yields and purity of the product, and offer no distinct advantages. At the preferred reaction temperatures the reaction is complete in about one-half to three hours.

On completion of the reaction the mixture is quenched in cold 5% hydrochloric acid and the product filtered or extracted with a water immiscible solvent, such as methylene chloride. The product remaining after removal of the extracting solvent or that obtained by filtration can be purified by conventional means, or can be employed in the preparation of piroxicam without further purification.

A preferred feature of this process is the use of those reagents wherein X is chloro, the reaction-inert solvent in dimethylformamide or dimethylsulfoxide and the metal hydride is sodium hydroxide.

Especially preferred is the preparation of products by this process wherein $R_1$ is methoxy and 2-methoxyethoxy.

The starting reagents for the second process of the present invention are readily prepared by reacting one mole of N-methylsaccharin with one mole of an appropriate haloacetate in the presence of two equivalents of a metal hydride, such as sodium hydride, in a reaction-inert solvent such as tetrahydrofuran as follows:

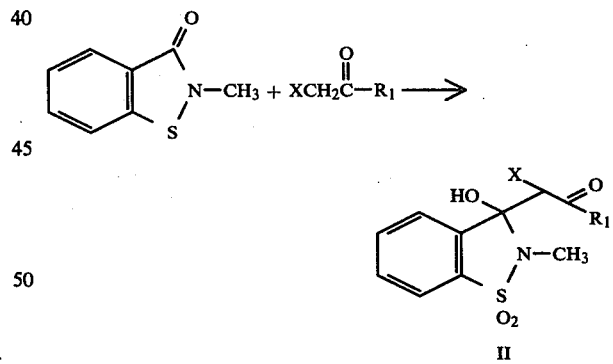

II

In practice a solution of N-methylsaccharin in tetrahydrofuran is treated with two equivalents of sodium hydride and the resulting reaction mixture warmed to about 40° C. The requisite alkyl or 2-methoxyethyl haloacetate is added over a period of about one hour, and the reaction mixture heated for several hours at 40°–50° C. following the completion of the addition. On completion of the reaction the mixture is added to a cold 5% hydrochloric acid solution, and the alkyl or 2-methoxyethyl 2-(2-methyl-3-hydroxy-2,3-dihydro-1,2-benzisosulfonazol-3-yl)-2-haloacetate either filtered and dried or extracted with a water immiscible solvent such as methylene chloride. If necessary, the product can be purified by conventional means.

Also considered as part of the present invention are certain 2-(2-methyl-3-hydroxy-2,3-dihydro-1,2-benzisosulfonazol-3-yl)-2-haloacetate esters which are useful as intermediates in the second process of the present invention.

Preferred are those compounds of formula II wherein X is chloro. Especially preferred are methyl 2-(2-methyl-3-hydroxy-2,3-dihydro-1,2-benzisosulfonazol-3-yl)-2-chloroacetate and 2-methoxyethyl 2-(2-methyl-3-hydroxy-2,3-dihydro-1,2-benzisosulfonazol-3-yl)-2-chloroacetate.

Aside from the known antiinflammatory agent piroxicam, the other products of the processes of the present invention are useful intermediates leading to piroxicam by preparatory methods described herein and/or described in the herein cited literature and patent references.

The following examples are provided solely for the purpose of further illustration. Nuclear magnetic resonance spectra (NMR) were measured at 60 MHz for solutions in deuterochloroform (CDCl$_3$), perdeutero dimethyl sulfoxide (DMSO-d$_6$) or deuterium oxide (D$_2$O) or are noted otherwise, and peak positions are expressed in parts per million (ppm) downfield from tetramethylsilane or sodium 2,2-dimethyl-2-silapentane-5-sulfonate. The following abbreviations for peak shapes are used: s, singlet; d, doublet; t, triplet; q, quartet; m, multiplet.

EXAMPLE 1

2-Methoxyethyl 4-hydroxy-2-methyl-2H-1,2-benzothiazine-3-carboxylate 1,1-dioxide (I; Y=—OCH$_2$CH$_2$OCH$_3$)

A. 2-methoxyethyl 2-chloroacetate

Maintaining a temperature of $-5°$ to $5°$ C., 2-chloroacetyl chloride (11.2 g., 0.10 mole) in 15 ml. of methylene chloride was added dropwise over 1 hour to a cold solution of pyridine (8.0 g., 0.11 mole) and 2-methoxyethanol (7.6 g., 0.10 mole) in 35 ml. of methylene chloride. The reaction mixture was stirred for a further 1 hour at 0° C., warmed to room temperature and extracted with two 50 ml. portions of water. The two aqueous extracts were combined and back-washed with 50 ml. of chloroform. The original organic layer and chloroform back-wash were combined and washed with 50 ml. of 5% copper sulfate. The 5% copper sulfate wash was back-washed with 25 ml. of chloroform and recombined with the organic phase. Finally, the organic phase was washed with 50 ml. of brine, treated with activated carbon and anhydrous magnesium sulfate, filtered, concentrated to an oil and distilled to yield 2-methoxyethyl 2-chloroacetate (14.1 g.; b.p. 80°–82° C.).

B. 2-methoxyethyl 4-hydroxy-2-methyl-2H-1,2-benzothiazine-3-carboxylate 1,1-dioxide To a solution of 3.0 g. (0.015 mole) of N-methylsaccharin and 2.3 g. (0.015 mole) of 2-methoxyethyl chloroacetate in 15 ml. of dimethylsulfoxide at 40° C. was added 810 mg. (0.033 mole) of sodium hydride over a 2 hour period. The resulting reaction mixture was stirred for 2 hours at 40°–50° C. and was then quenched in 5% hydrochloric acid solution. The resulting suspension was extracted with methylene chloride (2×100 ml.) and the organic layers separated, combined and washed with water (50 ml.) and a brine solution (50 ml). The organic layer was dried over magnesium sulfate and concentrated to an oil, 4.1 g. The product was purified by dissolution of the residue in 5 ml. of acetone and addition of the acetone slowly to 125 ml. of 0.25N hydrochloric acid. The suspension was allowed to stir for several hours, and was then filtered and dried 2.6 g. (55%). The product is indistinguishable from that reported in U.S. patent application Ser. No. 191,716, filed Sept. 29, 1980.

EXAMPLE 2

4-Hydroxy-2-methyl-N-2-pyridyl-2H-1,2-benzothiazine-3-carboxamide 1,1-Dioxide (Piroxicam)

2-Methoxyethyl 4-hydroxy-2H-1,2-benzothiazine-3-carboxylate 1,1-dioxide (28 g., 0.089 mole) and 2-aminopyridine (9.26 g., 0.098 mole) were combined with 500 ml. of xylene in a 1 liter flask equipped with an addition funnel and a reflux, variable take-off distillation head. The stirred reaction mixture was heated to reflux and the xylene distilled at the rate of approximately 100 ml./hour, while maintaining the pot volume almost constant by the addition of fresh xylene. After 6 hours, the head temperature, which had been relatively constant at 134° C., rose to 142° C. and reflux rate slowed. The reaction mixture was then cooled in an ice-bath and the precipitated solids recovered by filtration, with hexane for transfer and wash, and dried at 45° C. in vacuo to yield piroxicam (28.5 g., 96%; m.p. 167°–174° C.).

For purposes of recrystallization, the above piroxicam (25 g.) was taken up in 190 ml. of dimethylacetamide at 70°–75° C., treated with 1.26 g. of activated carbon at 75°–80° C. and filtered through diatomaceous earth with 55 ml. of warm dimethylacetamide for transfer and wash. A mixture of 173 ml. of acetone and 173 ml. of water was cooled to 510° C. The carbon-treated filtrate was added slowly over 10–15 minutes to the chilled aqueous acetone, and the resulting crystals granulated at 0°–5° C. for 5 minutes. Recrystallized piroxicam was recovered by filtration with 154 ml. of cold methanol for transfer and wash. Yield: 18.75 g., 75%; ir(nujol mull) identical with authentic piroxicam.

EXAMPLE 3

2-Methoxyethyl 4-hydroxy-2-methyl-2H-1,2-benzothiazine-3-carboxylate 1,1-dioxide (I; Y=OCH$_2$CH$_2$OCH$_3$)

In a manner similar to Example 1B, 1.0 g. of 91% sodium hydride was added over a period of one hour to a solution of 3.0 g. (0.015 mole) of N-methylsaccharin and 2.6 g. (0.017 mole) of 2-methoxyethyl chloroacetate in 15 ml. of dimethylformamide at 35° C. The exothermic reaction (55° C.) was allowed to stir for 2 hours after the addition was complete, and was then quenched in 5% hydrochloric acid solution and the product extracted with methylene chloride. The residue, remaining after the solvent was removed, was dissolved in 10 ml. of warm dimethylformamide and added to 100 ml. of 2% hydrochloric acid. The cooled suspension was stirred for 30 minutes and filtered. Drying of the filtered material gave 1.12 g. (24%) of the product identical with that prepared in Example 1B.

EXAMPLE 4

In a manner similar to Examples 1B and 3, 864 mg. of 99% sodium hydride was added over a period of one hour to 3.0 g. (0.015 mole) of N-methylsaccharin and 6.0 g. (0.03 mole) of methoxyethyl bromoacetate in 20 ml. of dimethylformamide. The reaction mixture was heated to 40°–45° C. for 3 hours and was then allowed to stand at room temperature over a weekend. The reaction mixture was quenched in 150 ml. of 5% hydrochloric acid solution and the product filtered and dried 1.9 g. The product was used as an intermediate without further purification.

EXAMPLE 5

Starting with N-methylsaccharin and the indicated 2-methoxyethyl haloacetate, hydride, temperature, and solvent and following the procedure of Example 1B, 2-methoxyethyl 4-hydroxy-2-methyl-2H-1,2-benzothiazine-3-carboxylate 1,1-dioxide is prepared:

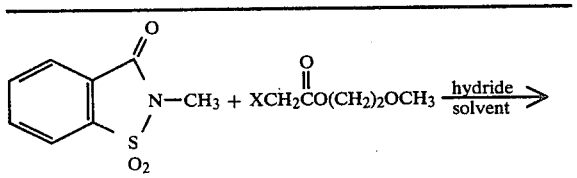

| X | Metal Hydride | Temp. °C. | Solvent |
|---|---|---|---|
| Cl | KH | 25 | DMSO[1] |
| Cl | KH | 50 | DMAC[2] |
| Cl | KH | 65 | HMPA[3] |
| Cl | CaH$_2$ | 70 | DMSO |
| Cl | NaH | 60 | 1-M-2-P[4] |
| Br | CaH$_2$ | 45 | DMF[5] |
| Br | KH | 25 | DMF |
| Br | NaH | 30 | HMPA |
| Br | CaH$_2$ | 55 | DMAC |
| Br | CaH$_2$ | 65 | DMSO |
| I | NaH | 50 | DMF |
| I | NaH | 60 | DMSO |
| I | KH | 50 | 1-M-2-P |
| I | KH | 65 | HMPA |
| I | CaH$_2$ | 70 | DMF |
| I | NaH | 60 | 1-M-2-P |

[1]DMSO = dimethylsulfoxide
[2]DMAC = dimethylacetamide
[3]HMPA = hexamethylphosphoramide
[4]1-M-2-P = 1-methyl-2-pyrrolidone
[5]DMF = dimethylformamide

EXAMPLE 6

Methyl 4-hydroxy-2-methyl-2H-1,2-benzothiazine-3-carboxylate 1,1-dioxide (I; Y=OCH$_3$)

To a solution of 2.9 g. (0.015 mole) of N-methylsaccharin and 2.63 g. (0.03 mole) of methylchloroacetate in 10 ml. of dimethylformamide at 40° C. was added over a period of two hours 864 mg. (0.036 mole) of 99% sodium hydride. Stirring was continued for two hours, maintaining a reaction temperature of 40°–50° C. The reaction mixture was quenched in 150 ml. of 5% hydrochloric acid, and the precipitated product filtered and dried, 3.41 g. (84%).

The product was identical from that reported in U.S. Pat. No. 3,591,584.

EXAMPLE 7

Methyl 4-hydroxy-2-methyl-2H-1,2-benzothiazine-3-carboxylate 1,1-dioxide (I; Y=OCH$_3$)

In a manner similar to Example 6, 864 mg. (0.036 mole) of 99% sodium hydride was added over a two hour period to a solution of 2.9 g. (0.015 mole) of N-methylsaccharin and 9.8 g. (0.09 mole) of methylchloroacetate in 10 ml. of dimethylsulfoxide at 40° C. Stirring was continued at 40°–45° C. for an additional two hours, and the reaction mixture was poured into 150 ml. of 5% hydrochloric acid solution. The precipitate was filtered and dried to give 3.07 (76%) of the desired product.

EXAMPLE 8

Employing the procedure of Example 6 and starting with N-methylsaccharin and the indicated alkyl haloacetate, hydride, reaction temperature and solvent the appropriate alkyl 4-hydroxy-2-methyl-2H-1,2-benzothiazine-3-carboxylate 1,1-dioxide is prepared:

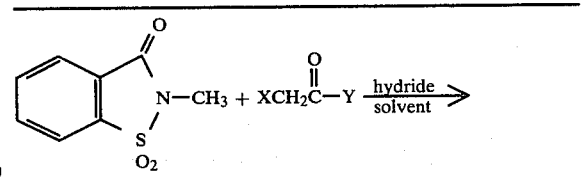

| X | Y | Metal hydride | Temp. °C. | Solvent |
|---|---|---|---|---|
| Cl | —OCH$_2$CH$_3$ | KH | 45 | DMF[1] |
| Cl | —O(CH$_2$)$_2$CH$_3$ | NaH | 50 | DMF |
| Cl | —OCH(CH$_3$)$_2$ | CaH$_2$ | 60 | DMSO[2] |
| Cl | —OCH$_3$ | CaH$_2$ | 70 | HMPA[3] |
| Cl | —O(CH$_2$)$_3$CH$_3$ | NaH | 30 | DMAC[4] |
| Cl | —OC(CH$_3$)$_3$ | KH | 45 | DMF |
| Cl | —OCH$_2$CH(CH$_3$)$_2$ | NaH | 45 | 1-M-2-P[5] |
| Br | —OCH$_2$ | NaH | 25 | DMF |
| Br | —OCH$_2$CH$_3$ | NaH | 45 | DMF |
| Br | —O(CH$_2$)$_2$CH$_3$ | KH | 45 | DMSO |
| Br | —O(CH$_2$)$_2$CH$_3$ | CaH$_2$ | 70 | DMAC |
| Br | —O(CH$_2$)$_3$CH$_3$ | KH | 60 | 1-M-2-P |
| Br | —OCH$_2$CH(CH$_3$)$_2$ | NaH | 45 | DMSO |
| I | —OCH$_3$ | NaH | 45 | DMF |
| I | —OCH$_2$CH$_3$ | KH | 60 | DMAC |
| I | —OCH(CH$_3$)$_2$ | KH | 35 | DMSO |
| I | —O(CH$_2$)$_3$CH$_3$ | NaH | 40 | HMPA |
| I | —OCH$_2$CH(CH$_3$)$_2$ | CaH | 70 | DMSO |
| I | —OC(CH$_3$)$_3$ | NaH | 45 | DMAC |

[1]DMF = dimethylformamide
[2]DMSO = dimethylsulfoxide
[3]HMPA = hexamethylphosphoramide
[4]DMAC = dimethylacetamide
[5]1-M-2-P = 1-methyl-2-pyrrolidone

EXAMPLE 9

4-Hydroxy-2-methyl-N-2-pyridyl-2H-1,2-benzothiazine-3-carboxamide 1,1-dioxide (Y=—NHC$_5$H$_4$N) (Piroxicam)

A. N-(2-pyridyl)chloroacetamide

To a solution of 9.42 g. (0.1 mole) of 2-aminopyridine in 50 ml. of methylene chloride was added dropwise 4.0 ml. (0.05 mole) of chloroacetyl chloride in 20 ml. of the same solvent, keeping the reaction temperature at −20° to −10° C. for one hour. After stirring at room temperature for 10 hours, 50 ml. of water was added and the organic layer separated. The organic solution was washed with water and a brine solution and was dried over magnesium sulfate. Removal of the solvent in vacuo gave 6.64 g. (78%), m.p. 114°–117° C., of the desired product.

A small sample was purified for analysis by recrystallization from acetonitrile, m.p. 122° C.

The NMR (CDCl$_3$) spectrum showed absorption at 9.0 (s, 1H), 8.4–6.9 (m, 4H) and 4.15 (s, 2H) ppm.

B.
4-hydroxy-2-methyl-N-2-pyridyl-2H-1,2-benzothiazine-3-carboxamide 1,1-dioxide (Y=NHC$_5$H$_4$N) (Piroxicam)

To a solution of 590 mg. (3 mmole) of N-methylsaccharin and 1.02 g. (6 mmole) of N-(2-pyridyl)-chloroacetamide in 3 ml. of dimethylformamide at 40° C. was added 250 mg. (10.3 mmole) of 99% sodium hydride portionwise over a period of one hour. The reaction mixture was allowed to stir at 40° C. for 2.5 hours and was then added to 100 ml. of 5% hydrochloric acid solution and 300 ml. of ice. The precipitate was filtered and dried to give 24 mg.

The filtrate was extracted with methylene chloride (6×50 ml.) and the extracts are combined, washed with water and a brine solution and dried over magnesium sulfate. Removal of the solvent gave 400 mg. of crude product. The product was identified by thin-layer chromatography and high-pressure liquid chromatography.

EXAMPLE 10

Employing the procedure of Example 9, and starting with N-methylsaccharin and the indicated N-(2-pyridyl)haloacetamide, hydride, temperature and solvent, 4-hydroxy-2-methyl-N-2-pyridyl-2H-1,2-benzothiazine-3-carboxamide 1,1-dioxide (Piroxicam) is prepared:

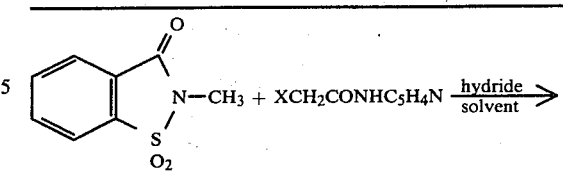

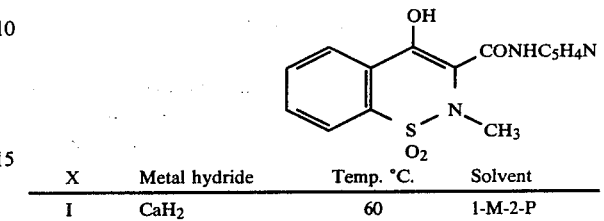

| X  | Metal hydride | Temp. °C. | Solvent |
|----|---------------|-----------|---------|
| Cl | KH            | 50        | DMSO[1] |
| Cl | KH            | 70        | DMAC[2] |
| Cl | CaH$_2$       | 60        | DMAC    |
| Cl | NaH           | 45        | HMPA[3] |
| Cl | NaH           | 25        | 1-M-2-P[4] |
| Br | NaH           | 40        | DMF[5]  |
| Br | NaH           | 50        | DMAC    |
| Br | KH            | 40        | DMF     |
| Br | CaH$_2$       | 70        | DMSO    |
| Br | CaH$_2$       | 60        | HMPA    |
| I  | NaH           | 45        | DMF     |
| I  | KH            | 55        | DMAC    |
| I  | KH            | 25        | DMF     |
| I  | CaH$_2$       | 60        | 1-M-2-P |

[1] DMSO = dimethylsulfoxide
[2] DMAC = dimethylacetamide
[3] HMPA = hexamethylphosphoramide
[4] 1-M-2-P = 1-methyl-2-pyrrolidone
[5] DMF = dimethylformamide

EXAMPLE 11
2-Methoxyethyl 4-hydroxy-2-methyl-2H-1,2-benzothiazine-3-carboxylate 1,1-dioxide (I; Y=—OCH$_2$CH$_2$OCH$_3$)

A. 2-methoxyethyl 2-(2-methyl-3-hydroxy-2,3-dihydro-1,2-benzisosulfonazol-3-yl)-2-chloroacetate (II; X=Cl, R$_1$=OCH$_2$CH$_2$OCH$_3$)

In a flame dried flask under a nitrogen atmosphere was placed 11.6 g. (0.24 mole) of 50% sodium hydride in an oil dispersion. The mineral oil was then removed by pentane washing and decantation, and 50 ml. of dry tetrahydrofuran was added. To the resulting suspension was added 20 g. (0.1 mole) of N-methylsaccharin in 30 ml. of the same solvent and the mixture heated to 40° C. 2-Methoxyethyl chloroacetate (15.4 g., 0.1 mole) was added to the reaction mixture dropwise over a period of one hour. The reaction was maintained at 40°–50° C. for two hours following the completion of the addition. The reaction was then quenched slowly into a cooled, well stirred 5% hydrochloric acid solution and the resulting precipitate extracted (4×100 ml.) with methylene chloride. The extracts were combined, dried over magnesium sulfate and concentrated in vacuo to give the crude desired product as a yellow oil, 37.6 g.

The crude product was crystallized from methylene chloride-hexane to give 22.75 g. (65%) of the product, m.p. 125.5°–126.5° C. A sample was further purified by recrystallizing from methylene chloride-hexane, m.p. 133°–135.5° C.

The NMR spectrum (DMSO-d$_6$) showed absorption at 7.6–8.2 (m, 5H), 5.1 (s, 1H), 4.0 (m, 2H), 3.3 (m, 2H), 3.1 (s, 3H) and 2.7 (s, 3H) ppm.

Anal. Calcd. for C$_{13}$H$_{16}$O$_6$SNCl: C, 44.6; H, 4.6; N, 4.0. Found: C, 44.3; H, 4.7; N, 4.0.

B. 2-methoxyethyl 4-hydroxy-2-methyl-2H-1,2-benzothiazine-3-carboxylate 1,1-dioxide To 280 mg. (5.8 mmole) of 50% sodium hydride dispersion which had been washed with pentane was added 10 ml. of dimethylsulfoxide at room temperature. To the resulting suspension was added 1.75 g. (5 mmole) of 2-methoxyethyl 2-(2-methyl-3-hydroxy-2,3-dihydro- 1,2-benzisosulfonazol-3-yl)-2-chloroacetate. The reaction mixture, which rose in temperature to 32° C. was allowed to stir for 1.5 hours, and was then added to 150 ml. of a cold 5% hydrochloric acid solution. The precipitate was filtered and dried, 1.29 g. (82.4%).

The NMR spectrum (DMSO-$d_6$) showed absorption at 8.0 (m, 4H), 4.5 (m, 2H), 3.7 (m, 2H), 3.34 (s, 3H) and 2.90 (s, 3H) ppm.

The product is indistinguishable from that reported in Example 1 and U.S. patent application Ser. No. 191,716, filed Sept. 29, 1980.

EXAMPLE 12

A. Following the procedure of Example 11A, and starting with N-methylsaccharin and 2-methoxyethyl bromo- and iodoacetates, 2-methoxyethyl 2-(2-methyl-3-hydroxy-2,3-dihydro-1,2-benzisosulfonazol-3-yl)-2-bromoacetate and 2-methoxyethyl 2-(2-methyl-3-hydroxy-2,3-dihydro-1,2-benzisosulfonazol-3-yl)-2-iodoacetate are prepared, respectively.

B. Starting with the indicated 2-methoxyethyl 2-(2-methyl-3-hydroxy-2,3-dihydro-1,2-benzisosulfonazol-3-yl)-2-haloacetate, hydride, solvent and temperature, and employing the procedure of Example 11B, 2-methoxyethyl 4-hydroxy-2-methyl-2H-1,2-benzothiazine-3-carboxylate 1,1-dioxide is prepared:

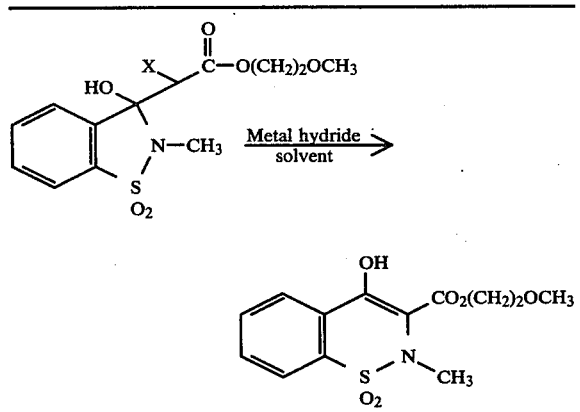

| X  | Metal hydride | Temp. °C. | Solvent |
|----|---------------|-----------|---------|
| Cl | KH            | 25        | DMF[1]  |
| Cl | CaH$_2$       | 45        | DMF     |
| Cl | NaH           | 35        | DMAC[2] |
| Cl | NaH           | 50        | 1-M—2-P[3] |
| Cl | KH            | 50        | HMPA[4] |
| Cl | KH            | 40        | DMF     |
| Br | NaH           | 35        | DMAC    |
| Br | NaH           | 35        | DMSO[5] |
| Br | KH            | 25        | DMF     |
| Br | CaH$_2$       | 50        | DMAC    |
| Br | CaH$_2$       | 50        | DMSO    |
| Br | KH            | 30        | HMPA    |

[1]DMF = dimethylformamide
[2]DMAC = dimethylacetamide
[3]1-M—2-P = 1-methyl-2-pyrrolidone
[4]HMPA = hexamethylphosphoramide
[5]DMSO = dimethylsulfoxide

EXAMPLE 13

Methyl 4-hydroxy-2-methyl-2H-1,2-benzothiazine-3-carboxylate 1,1-dioxide (I; Y=OCH$_3$)

A. methyl 2-(2-methyl-3-hydroxy-2,3-dihydro-1,2-benzisosulfonazol-3-yl)-2-chloroacetate (II; R$_1$=OCH$_3$)

To 9.2 g. (0.19 mole) of a 50% sodium hydride-oil dispersion, which had been washed free of oil with pentane, was added under a nitrogen atmosphere 20 ml. of dry tetrahydrofuran. To the resulting suspension was added 15.9 g. (0.08 mole) of N-methylsaccharin in 50 ml. of the same solvent and the slurry heated to 40° C. Methyl chloroacetate (7 ml., 0.08 mole) in 20 ml. of dry tetrahydrofuran was added over a period of one hour, keeping the reaction temperature at 40°–45° C. Following the completion of the addition the reaction mixture was allowed to stir at 35°–42° C. for 4 hours. The reaction mixture was then quenched in 700 ml. of a 5% hydrochloric acid solution and the product extracted with methylene chloride (7×100 ml.). The combined extracts were washed with a 5% hydrochloric acid solution and a saturated brine solution, and dried over magnesium sulfate. Removal of the solvent in vacuo gave 21 g. of the product as a heavy oil which solidified on standing.

A portion was triturated with isopropanol to give a white solid, m.p. 122°–125° C.

The NMR spectrum (DMSO-$d_6$) showed absorption at 8.1–7.6 (m, 5H), 5.05 (s, 1H), 3.45 (s, 3H) and 2.7 (s, 3H) ppm.

Anal. Calcd. for C$_{11}$H$_{12}$O$_5$NSCl: C, 43.2; H, 3.9; N, 4.6. Found: C, 43.1; H, 4.0; N, 4.6.

B. methyl 4-hydroxy-2-methyl-2H-1,2-benzothiazine-3-carboxylate 1,1-dioxide

To 63 mg. (0.0013 mole) of sodium hydride washed free of oil with pentane in 8 ml. of dry dimethylsulfoxide was added 400 mg. (0.0013 mole) of methyl 2-(2-methyl-3-hydroxy-2,3-dihydro-1,2-benzisosulfonazol-3-yl)-2-chloroacetate in 8 ml. of dimethylsulfoxide. The reaction mixture was heated at 35° C. for one hour and fifteen minutes and was then quenched in 80 ml. of a cold 5% hydrochloric acid solution. The precipitate was filtered and dried to give 280 mg. (80%) of the desired product, m.p. 162°–163° C. The product was undistinguishable from that reported in U.S. Pat. No. 3,591,584 and Examples 6 and 7.

EXAMPLE 14

A. Following the procedure of Example 13A, and starting with N-methylsaccharin and the appropriate alkyl haloacetate the following 1,2-benzisosulfonazoles are prepared:

| X  | R$_1$       |
|----|-------------|
| Cl | —OCH$_2$CH$_3$ |

-continued

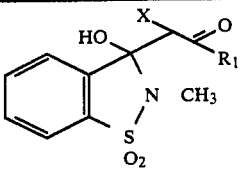

| X  | R₁            |
|----|---------------|
| Cl | —O(CH₂)₂CH₃   |
| Cl | —OCH(CH₃)₂    |
| Cl | —O(CH₂)₃CH₃   |
| Cl | —OC(CH₃)₃     |
| Cl | —OCH₂CH(CH₃)₂ |
| Br | —OCH₃         |
| Br | —OCH₂CH₃      |
| Br | —O(CH₂)₂CH₃   |
| Br | —O(CH₂)₃CH₃   |
| Br | —OCH₂CH(CH₃)₂ |
| I  | —OCH₃         |
| I  | —OCH₂CH₃      |
| I  | —OCH(CH₃)₂    |
| I  | —O(CH₂)₃CH₃   |
| I  | —OCH₂CH(CH₃)₂ |
| I  | —OC(CH₃)₃     |

B. Following the procedure of Example 13B, and employing with the indicated 1,2-benzisosulfonazole, hydride, reaction temperature and solvent the appropriate alkyl 4-hydroxy-2-methyl-2H-1,2-benzothiazine-3-carboxylate 1,1-dioxide is prepared:

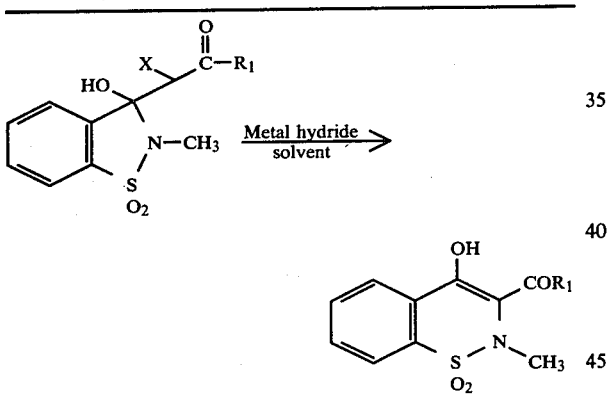

| X  | R₁            | Metal hydride | Temp. °C. | Solvent |
|----|---------------|---------------|-----------|---------|
| Cl | —OCH₃         | KH            | 25        | DMF[1]  |
| Cl | —OCH₂CH₃      | NaH           | 30        | DMAC[2] |
| Cl | —O(CH₂)₂CH₃   | NaH           | 35        | DMF     |
| Cl | —OCH(CH₃)₂    | CaH₂          | 50        | DMSO[3] |
| Cl | —O(CH₂)₃CH₃   | NaH           | 45        | DMAC    |
| Cl | —OC(CH₃)₃     | KH            | 30        | HMPA[4] |
| Cl | —OCH₂CH(CH₃)₂ | KH            | 25        | 1-M—2-P[5] |
| Br | —OCH₃         | NaH           | 35        | DMF     |
| Br | —OCH₂CH₃      | KH            | 35        | DMF     |
| Br | —O(CH₂)₃CH₃   | KH            | 25        | DMAC    |
| Br | —O(CH₂)₂CH₃   | CaH₂          | 45        | DMSO    |
| Br | —OCH₂CH(CH₃)₂ | NaH           | 50        | 1-M—2-P |
| I  | —OCH₃         | KH            | 40        | DMF     |
| I  | —OCH₂CH₃      | NaH           | 40        | HMPA    |
| I  | —OCH(CH₃)      | KH            | 35        | DMSO    |
| I  | —(CH₂)₃CH₃    | CaH₂          | 50        | DMSO    |
| I  | —OCH₂CH(CH₃)  | NaH           | 30        | DMAC    |
| I  | —OC(CH₃)₃     | KH            | 25        | DMF     |

[1] DMF = dimethylformamide
[2] DMAC = dimethylacetamide
[3] DMSO = dimethylsulfoxide
[4] HMPA = hexamethylphosphoramide
[5] 1-M—2-P = 1-methyl-2-pyrrolidone

EXAMPLE 15

Methyl 4-hydroxy-2-methyl-2H-1,2-benzothiazine-3-carboxylate 1,1-dioxide (I; Y=OCH₃)

To 27 ml. of dimethylsulfoxide containing 5.18 g. (26.3 mmoles) of N-methylsaccharin and 4.6 ml. (52.5 mmoles) of methyl chloroacetate at 25° C. was added 14.1 g. (126 mmoles) of potassium t-butoxide in 44 ml. of the same solvent at the rate of 0.1 ml. every minute. After 42.2 ml. of the potassium t-butoxide solution had been added the addition was stopped. During the addition the reaction temperature was maintained at about 30°–32° C.

After the addition was complete the reaction mixture was allowed to stir at 30° C. for 10 minutes. The reaction mixture was quenched in 262 ml. of 5% hydrochloric acid at 25° C., and the precipitated product was filtered, washed with water and dried, 6.53 g.

EXAMPLE 16

Methyl 4-hydroxy-2-methyl-2H-1,2-benzothiazine-3-carboxylate 1,1-dioxide (I; Y=OCH₃)

To a solution of 9.86 g. (50 mmoles) of N-methylsaccharin and 10.8 ml. of methyl chloroacetate (123.8 mmoles) in 50 ml. of dimethylsulfoxide was added at the rate of 0.15 ml./minute 9.2 g. (170 mmoles) of sodium methoxide in 30 ml. of methanol. After the addition was complete an additional 2.7 g. (50 mmoles) of sodium methoxide in 11 ml. of methanol was added at the same rate for a total addition time of about 6 hours.

The reaction mixture was added to 800 ml. of 0.25N hydrochloric acid, and the precipitated product filtered, washed with water and dried, 3.8 g.

EXAMPLE 17

Methyl 4-hydroxy-2-methyl-2H-1,2-benzothiazine-3-carboxylate 1,1-dioxide (I; Y=OCH₃)

In a manner similar to Examples 15 and 16, to a solution of 2.86 g. (50 mmoles) of N-methylsaccharin and 10.8 ml. (100 mmoles) of methyl chloroacetate in 17 ml. of dimethylsulfoxide was added 11.56 g. (170 mmoles) of sodium ethoxide in 63 ml. of dimethylsulfoxide over a period of 2.5 hours.

The reaction mixture wwas added to 800 ml. of 0.25N hydrochloric acid, and the precipitated product filtered, washed with water and dried, 3.0 g.

EXAMPLE 18

Starting with N-methylsaccharin and the indicated ester, alkoxide, temperature and solvent, and employing the procedure of Example 17, the following 4-hydroxy-2-methyl-2H-1,2-benzothiaizne-3-carboxylate 1,1-dioxide esters are prepared:

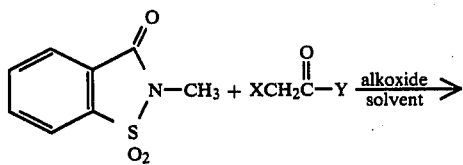 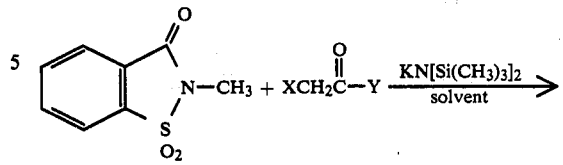

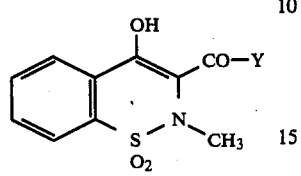 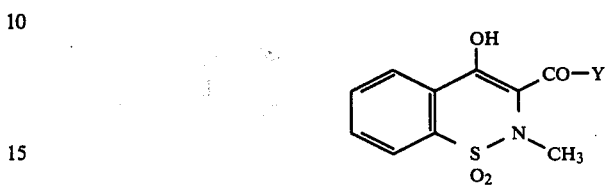

| X | Y | Alkoxide | Temp. °C. | Solvent |
|---|---|---|---|---|
| Cl | $OC_2H_5$ | KO—t-$C_4H_9$ | 35 | DMSO[1] |
| Cl | $OC_3H_7$ | $NaOC_2H_5$ | 40 | DMAC[2] |
| Cl | $OCH_3$ | KO—i-$C_3H_7$ | 30 | HMPA[3] |
| Cl | O—n-$C_4H_9$ | Na—n-$C_4H_9$ | 45 | DMSO |
| Cl | $OCH_3$ | KO—t-$C_4H_9$ | 60 | 1-M—2-P[4] |
| Br | $OCH_3$ | $NaOCH_3$ | 25 | DMF[5] |
| Br | O—n-$C_3H_7$ | $NaOC_2H_5$ | 35 | DMF |
| Br | $O(CH_2)_2OCH_3$ | KO—t-$C_4H_9$ | 30 | DMSO |
| Br | $OC_2H_5$ | $NaOC_2H_5$ | 35 | DMF |
| Br | $OC_2H_5$ | $NaOC_2H_5$ | 30 | 1-M—2-P |
| I | $OCH_3$ | $NaOCH_3$ | 30 | DMSO |
| I | $O(CH_2)_2OCH_3$ | KO—t-$C_4H_9$ | 30 | HMPA |
| I | $OC_2H_5$ | $LiOC_2H_5$ | 35 | DMF |
| I | O—n-$C_4H_9$ | $KOCH_3$ | 60 | 1-M—2-P |

[1]DMSO = dimethylsulfoxide
[2]DMAC = dimethylacetamide
[3]HMPA = hexamethylphosphoramide
[4]1-M—2-P = 1-methyl-2-pyrrolidone
[5]DMF = dimethylformamide

| X | Y | Temp. °C. | Solvent |
|---|---|---|---|
| Cl | $OCH_3$ | 35 | DMF[1] |
| Cl | $OC_2H_5$ | 45 | DMSO[2] |
| Cl | O—i-$C_3H_7$ | 30 | HMPA[3] |
| Cl | O—t-$C_4H_9$ | 35 | DMSO |
| Cl | O—i-$C_3H_7$ | 60 | DMAC[4] |
| Br | $OCH_3$ | 30 | 1-M—2-P[5] |
| Br | O—n-$C_3H_7$ | 30 | DMSO |
| Br | O—n-$C_4H_9$ | 40 | 1-M—2-P |
| Br | $OC_2H_5$ | 50 | DMF |
| Br | $O(CH_2)_2OCH_3$ | 30 | DMAC |
| I | $OCH_3$ | 30 | DMSO |
| I | $OC_2H_5$ | 30 | HMPA |
| I | O—n-$C_3H_7$ | 45 | 1-M—2-P |
| I | O—n-$C_4H_9$ | 45 | DMF |

[1]DMF = dimethylformamide
[2]DMSO = dimethylsulfoxide
[3]HMPA = hexamethylphosphoramide
[4]DMAC = dimethylacetamide
[5]1-M—2-P = 1-methyl-2-pyrrolidone

EXAMPLE 19

Methyl 4-hydroxy-2-methyl-2H-1,2-benzothiazine-3-carboxylate 1,1-dioxide (I; Y=$OCH_3$)

To 870 mg. (4.4 mmoles) of N-methylsaccharin and 0.95 ml. (10.89 mmoles) of methyl chloroacetate in 3 ml. of dimethylsulfoxide under nitrogen was added at the rate of 0.084 ml./minute 3.99 g. (20 mmoles) of potassium hexamethyl disilazane in 9.98 ml. of dimethylsulfoxide.

The reaction mixture was then quenched in 130 ml. of 1N hydrochloric acid, and the precipitated product was filtered, washed with water and dried, 1.05 g. The product was identical to that isolated in Example 6.

EXAMPLE 20

Employing the indicated starting reagents and reaction temperatures and following the procedure of Example 19, the following 4-hydroxy-2-methyl-2H-1,2-benzothiazine-3-carboxylate 1,1-dioxide esters are prepared:

EXAMPLE 21

Methyl 4-hydroxy-2-methyl-2H-1,2-benzothiazine-3-carboxylate 1,1-dioxide (I; Y=$OCH_3$)

To a solution of 4.64 g. (23.5 mmoles) of N-methylsaccharin and 5.18 ml. (58.19 mmoles) of methyl chloroacetate in 20 ml. of dimethylsulfoxide was added at the rate of 0.3 ml./minute 13.9 g. (100 mmoles) of potassium diisopropylamine in 40 ml. of dimethylsulfoxide and 18 ml. of nonane.

When the addition was complete the reaction mixture was assayed by liquid chromatography. Using a standard sample of methyl 4-hydroxy-2-methyl-2H-1,2-benzothiazine-3-carboxylate 1,1-dioxide the yield of product was 67%.

EXAMPLE 22

Following the procedure of Example 21 and employing the indicated starting reagents and reaction temperature, the following 4-hydroxy-2-methyl-2H-1,2-benzothiazine-3-carboxylate 1,1-dioxide esters are prepared:

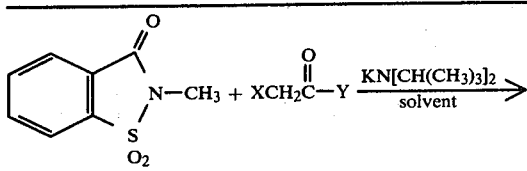

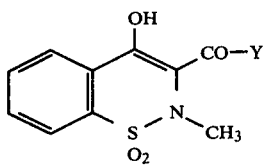

| X | Y | Temp. °C. | Solvent |
|---|---|---|---|
| Cl | OCH$_3$ | 40 | DMSO[1] |
| Cl | OC$_2$H$_5$ | 60 | DMAC[2] |
| Cl | O—n-C$_3$H$_7$ | 30 | DMSO |
| Cl | O—n-C$_3$H$_7$ | 35 | HMPA[3] |
| Cl | O—t-C$_4$H$_9$ | 35 | DMSO |
| Br | O(CH$_2$)$_2$OCH$_3$ | 35 | 1-M—2-P[4] |
| Br | OCH$_3$ | 60 | DMSO |
| Br | O—i-C$_3$H$_7$ | 70 | DMAC |
| Br | O—n-C$_4$H$_9$ | 45 | DMF[5] |
| Br | OCH$_3$ | 55 | DMSO |
| I | O(CH$_2$)$_2$OCH$_3$ | 60 | 1-M—2-P |
| I | OCH$_3$ | 25 | 1-M—2-P |
| I | OC$_2$H$_5$ | 25 | DMSO |

[1]DMSO = dimethylsulfoxide
[2]DMAC = dimethylacetamide
[3]HMPA = hexamethylphosphoramide
[4]1-M—2-P = 1-methyl-2-pyrrolidone
[5]DMF = dimethylformamide

I claim:

1. A process for preparing a compound selected from those of the formula

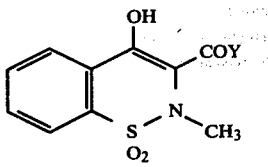

wherein Y is selected from the group consisting of alkoxy having from one to four carbon atoms, 2-methoxyethoxy and 2-pyridylimino which comprises reacting a compound of the formula

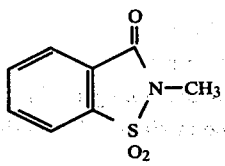

with a compound selected from those of the formula

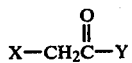

wherein X is selected from the group consisting of chloro, bromo and iodo in a polar, reaction-inert solvent in the presence of a base selected from the group consisting of at least two equivalents of a metal hydride, at least two equivalents of an alkali metal alkoxide having one to four carbon atoms, at least two equivalents of potassium hexamethyl disilazane and at least two equivalents of potassium diisopropylamine at a temperature of from about 25° to about 70° C. until the reaction is substantially complete.

2. The process of claim 1, wherein the polar reaction-inert solvent is selected from the group consisting of dimethylformamide, dimethylacetamide, dimethylsulfoxide, hexamethylphosphoramide and 1-methyl-2-pyrrolidone.

3. The process of claim 2, wherein the base is a metal hydride selected from the group consisting of potassium hydride, sodium hydride and calcium hydride.

4. The process of claim 3, wherein X is selected from the group consisting of chloro and bromo, the polar reaction-inert solvent is selected from the group consisting of dimethylsulfoxide and dimethylformamide and the metal hydride is sodium hydride.

5. The process of claim 4, wherein Y is methoxy.

6. The process of claim 4, wherein Y is 2-methoxyethoxy.

7. The process of claim 4, wherein Y is 2-pyridylimino.

8. The process of claim 2, wherein the base is potassium hexamethyl disilazane, Y is methoxy, X is chloro and the reaction-inert solvent is dimethylsulfoxide.

9. The process of claim 2, wherein the base is an alkali metal alkoxide having one to four carbon atoms.

10. The process of claim 9, wherein the base is potassium t-butoxide, X is chloro, Y is methoxy and the reaction-inert solvent is dimethylsulfoxide.

11. A process for preparing a compound selected from those of the formula

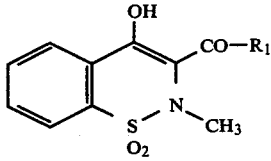

wherein R$_1$ is selected from the group consisting of alkoxy having one to four carbon atoms and 2-methoxyethoxy which comprises reacting a compound selected from those of the formula

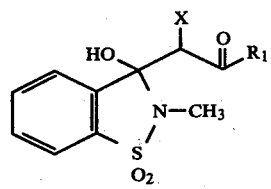

wherein X is selected from the group consisting of chloro, bromo and iodo with one equivalent of a metal hydride in a polar reaction-inert solvent at a temperature of from about 25° to about 50° C. until the reaction is substantially complete.

12. The process of claim 11, wherein the polar reaction-inert solvent is selected from the group consisting of dimethylformamide, dimethylacetamide, dimethylsulfoxide, hexamethylphosphoramide and 1-methyl-2-pyrrolidone.

13. The process of claim 12, wherein the metal hydride is selected from the group consisting of potassium hydride, sodium hydride and calcium hydride.

14. The process of claim 13, wherein X is chloro, the reaction-inert solvent is selected from the group consisting of dimethylsulfoxide and dimethylformamide and the metal hydride is sodium hydride.

15. The process of claim 14, wherein R$_1$ is methoxy.

16. The process of claim 14, wherein R$_1$ is 2-methoxyethoxy.

* * * * *